United States Patent
Viren (10) Patent No.: US 9,857,311 B2
(45) Date of Patent: Jan. 2, 2018

(54) METHODS AND SYSTEMS FOR NONDESTRUCTIVE TESTING WITH ACCURATE POSITION

(71) Applicant: GE-Hitachi Nuclear Energy Americas LLC, Wilmington, NC (US)

(72) Inventor: Robert W. Viren, Wilmington, NC (US)

(73) Assignee: GE-HITACHI NUCLEAR ENERGY AMERICAS LLC, Wilmington, NC (US)

( * ) Notice: Subject to any disclaimer, the term of this patent is extended or adjusted under 35 U.S.C. 154(b) by 526 days.

(21) Appl. No.: 14/470,855

(22) Filed: Aug. 27, 2014

(65) Prior Publication Data

US 2016/0061783 A1    Mar. 3, 2016

(51) Int. Cl.
*G01N 29/22* (2006.01)
*G01N 21/84* (2006.01)
*G01N 29/06* (2006.01)
*G01N 29/26* (2006.01)
(Continued)

(52) U.S. Cl.
CPC ......... *G01N 21/84* (2013.01); *G01N 21/8803* (2013.01); *G01N 29/0654* (2013.01); *G01N 29/225* (2013.01); *G01N 29/262* (2013.01); *G01N 29/265* (2013.01); *G01N 2291/044* (2013.01); *G01N 2291/102* (2013.01)

(58) Field of Classification Search
CPC .......................... G01N 29/225; G01N 29/226
See application file for complete search history.

(56) References Cited

U.S. PATENT DOCUMENTS

2009/0112094 A1    4/2009  Qin et al.
2010/0226541 A1*   9/2010  Kobayashi ......... G21C 17/013
                                                        382/106
(Continued)

FOREIGN PATENT DOCUMENTS

JP        03085069 A  *  4/1991
JP      2005315709 A  * 11/2005

OTHER PUBLICATIONS

Sun, 6-DOF Probe Tracking Via Skin Mapping for Freehand 3D Ultrasound, MIT Laboratory for and Manufacturing and Productivity, Cambridge, MA, USA.

*Primary Examiner* — Erika J Villaluna
(74) *Attorney, Agent, or Firm* — Ryan Alley IP (57) ABSTRACT

Inspection devices nondestructively sense component shape and integrity such as through ultrasonic sensors. Inspection devices include a positional determinator to give orientation of devices relative to the tested object. True distances and relative boundaries of the object are determined with testing and orientation data regardless of rigid or known inspection device position. Inspection data can be corrected for refraction knowing distances and object boundaries. Inspection devices can include additional inspection components like cameras and lighting to match visual inspection with nondestructive testing data spatially and temporally. Inspection devices can be used with self- or manual-propulsion in a working environment with the inspection object. Inspection devices use an operator or computer processor, local or remotely-connected power sources, and communications structures to power and operate the devices.

16 Claims, 4 Drawing Sheets

(51) Int. Cl.
G01N 29/265 (2006.01)
G01N 21/88 (2006.01)

(56) References Cited

U.S. PATENT DOCUMENTS

| | | |
|---|---|---|
| 2011/0000300 A1* | 1/2011 | Isobe .................. G01N 29/262 73/625 |
| 2011/0120223 A1 | 5/2011 | MacLauchlan et al. |
| 2011/0126626 A1 | 6/2011 | Koch et al. |
| 2013/0014587 A1 | 1/2013 | Yamamoto et al. |
| 2013/0197824 A1 | 8/2013 | Baba et al. |
| 2013/0220020 A1 | 8/2013 | Wigh et al. |
| 2014/0036633 A1 | 2/2014 | Oberdorfer |
| 2014/0060196 A1 | 3/2014 | Falter et al. |

* cited by examiner

METHODS AND SYSTEMS FOR NONDESTRUCTIVE TESTING WITH ACCURATE POSITION

BACKGROUND

Ultrasonic testing allows non-destructive verification of surfaces and interiors of various structures whose integrity may be important for operations and safety. Non-destructive testing is used throughout construction, power generation, and aeronautics industries in both manufacture/fabrication and during life of use, where various testing protocols and devices are used during maintenance, at set intervals, or following operations-impacting events. Ultrasonic testing in particular can be used by portable devices that use acoustic signals to determine a tested structure's integrity, shape, internal configuration, etc.

Figure 1:
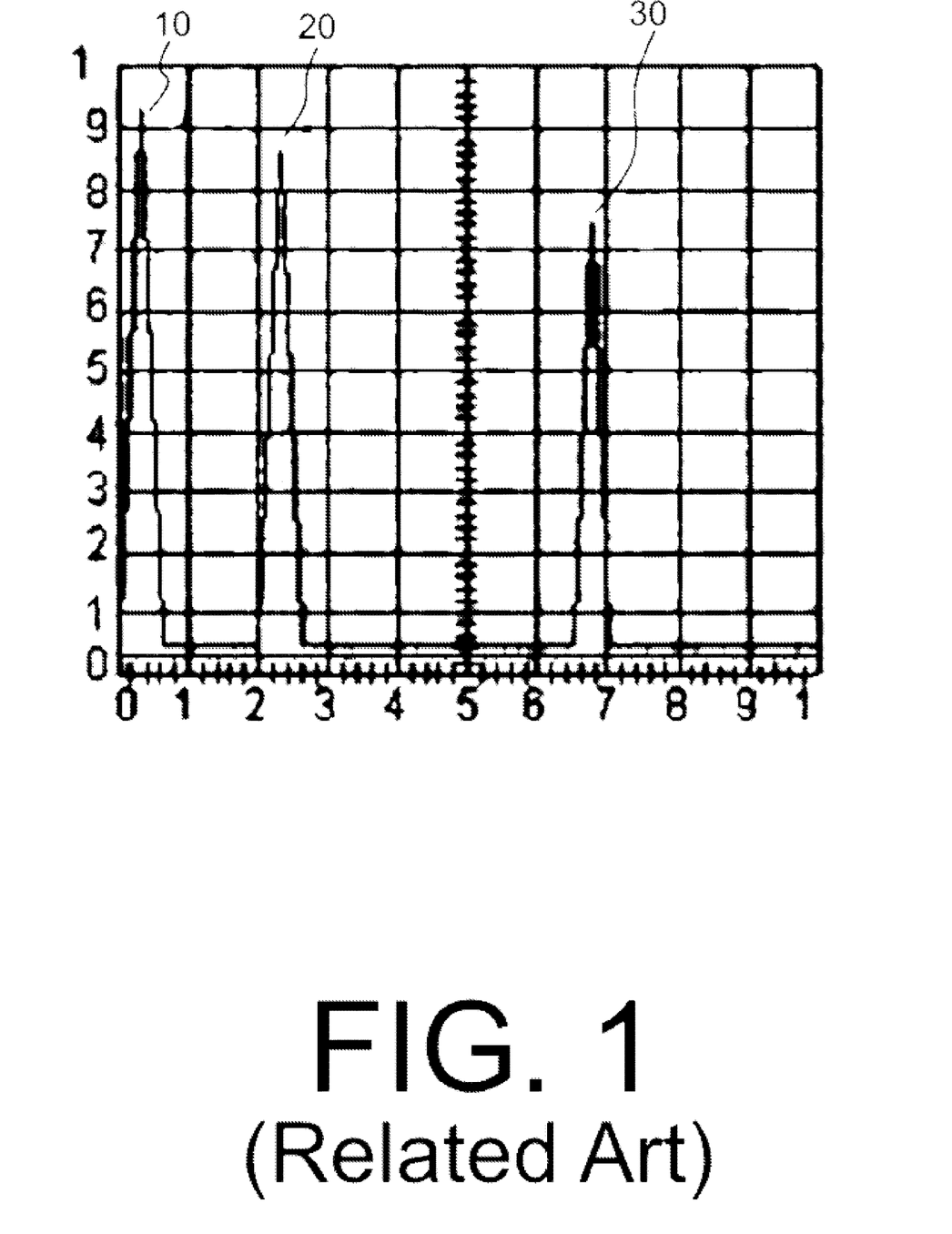
FIG. 1 is an illustration of a related art ultrasonic testing output.

FIG. 1 is an illustration of data that can be returned by an ultrasonic sensor that emits a discreet acoustic signal and detects its reflection in a tested structure. For example, the ultrasonic device may be a submerged sensor emitting acoustic signals, or pings, of a detectable frequency and amplitude in water that bounce off a tested object, such as a pipe wall or boat hull, also submerged. As shown in FIG. 1, the ultrasonic device may emit a ping at t=0, detected at first peak 10. A portion of the ping may bounce off a front wall of the tested structure and be detected later at t=2 at a second peak 20 upon returning to the sensor. Another portion of the ping may pass through the front wall of the tested structure to a back wall, where it is reflected back and detected at t=6.5 at a third peak 30. By comparing the different times and amplitudes between peaks 20 and 30, a user or program may determine the thickness of the wall using the known speed of the sound through the structure and water. By emitting and sensing ultrasonic pings with such a device in FIG. 1 at several different locations, a user or program can compare variations in wall thickness and detect potential abnormalities such as voids or cracks, as well as verify structure positioning and size, like a weld or wall position and depth.

Non-destructive testing can also include visual inspection, non-visual electromagnetic inspection (like x-ray inspection), radiographic inspection with beta radiation, magnetic resonance inspection, etc. In such testing, each result typically must be paired with a relatively accurate location of the tested structure in order to verify integrity and dimensions as expected locations as well as give accurate position of detected anomalies. Where a tested structure is inaccessible or difficult to visualize by a human operator or visually-verifying program, indirect methods of verifying tested structure location can be used. For example, a testing probe may be locked on a set of tracks at known positions to verify probe position and then verify tested structure position. Or a testing probe may be positioned at verifiable locations via RFID or optical tags to derive tested structure position. Still further, visual analysis, such as KLT stabilization, can be used to identify high contrast areas, shapes, and edges in order to approximate probe position from an image.

SUMMARY

Example embodiments include probes that can sense component shape and integrity without destroying the same by receiving reflected energy from the component that indicates the same. For example, a probe may include an ultrasonic sensor capable of receiving vibrational energy reflected from a test subject. The probe further includes a positional element to orient the probe relative to the object such that true distances and relative boundaries of the object can be determined. Through example methods, a processor or user may know true position of a probe and ultrasonic data with respect to an inspection subject without strict positional controls. An example embodiment probe can also include a video capture device, like a camera, to match visual inspection with nondestructive testing data by both true position and at same times. An example embodiment probe may also include a drive, like a propeller or jet or wheels or manual rod for user grappling, to move the probe freely about inspected objects without strict regard for position. A computer processor, and local power sources and wireless communications transceivers, and/or external power hookups and communications cables, can be used in example embodiment probes to power and operate the same, potentially remotely by users stationed in areas distant or unreachable from the inspected objects.

Example methods include receiving nondestructive testing data, like ultrasonic waves emitted and reflected back to an emitter and receiver, in a medium along with positional data of the receiver. Using the data, a closest point and orientation and distance of the point from the tester can be calculated. Testing may then iteratively advance to farther points from the determined closest point to map out a surface of the tested object. The nondestructive testing data may then be corrected where it falls at an interior of the object and thus refracts, and accurate position of all testing data may be known with respect to an object being tested, without a controlled, previously-known set position of a testing device and object being tested. The testing data and positional data may also be accurately paired with visual inspection data to give comprehensive, accurate visual and positional testing results

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the terms which they depict.

DETAILED DESCRIPTION

This is a patent document, and general broad rules of construction should be applied when reading and understanding it. Everything described and shown in this document is an example of subject matter falling within the scope of the appended claims. Any specific structural and functional details disclosed herein are merely for purposes of describing how to make and use example embodiments or methods. Several different embodiments not specifically disclosed herein fall within the claim scope; as such, the claims may be embodied in many alternate forms and should not be construed as limited to only example embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected," "coupled," "mated," "attached," or "fixed" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.). Similarly, a term such as "communicatively connected" includes all variations of information exchange routes between two devices, including intermediary devices, networks, etc., connected wirelessly or not.

As used herein, the singular forms "a", "an" and "the" are intended to include both the singular and plural forms, unless the language explicitly indicates otherwise with words like "only," "single," and/or "one." It will be further understood that the terms "comprises", "comprising,", "includes" and/or "including", when used herein, specify the presence of stated features, steps, operations, elements, ideas, and/or components, but do not themselves preclude the presence or addition of one or more other features, steps, operations, elements, components, ideas, and/or groups thereof.

It should also be noted that the structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, so as to provide looping or other series of operations aside from the single operations described below. It should be presumed that any embodiment having features and functionality described below, in any workable combination, falls within the scope of example embodiments.

The inventors have recognized that existing nondestructive testing devices often require stringent positional controls in order to properly correlate testing data with visual data and tested object location. These positional controls, like tracks, targets, RFID tags, and other equipment often require additional installation and encumber inspections in remote locations, like underwater. Moreover, strict positional controls often limit the degree to which inspections can be conducted, because a testing device cannot be freely moved to areas of interest while maintaining positional control or verification. To overcome these newly-recognized problems as well as others, the inventor has developed systems and methods that provide reliable and additional positional data during nondestructive testing such that strict positional controls may be reduced or forgone entirely. This may permit faster and less equipment-intensive installation and maintenance, as well as improve speed and flexibility in nondestructive testing.

The present invention is a nondestructive testing device that includes a positional element and uses testing data to determine relative locations without rigid position control or locking. In contrast to the present invention, the few example embodiments and example methods discussed below illustrate just a subset of the variety of different configurations that can be used as and/or in connection with the present invention.

Figure 2:
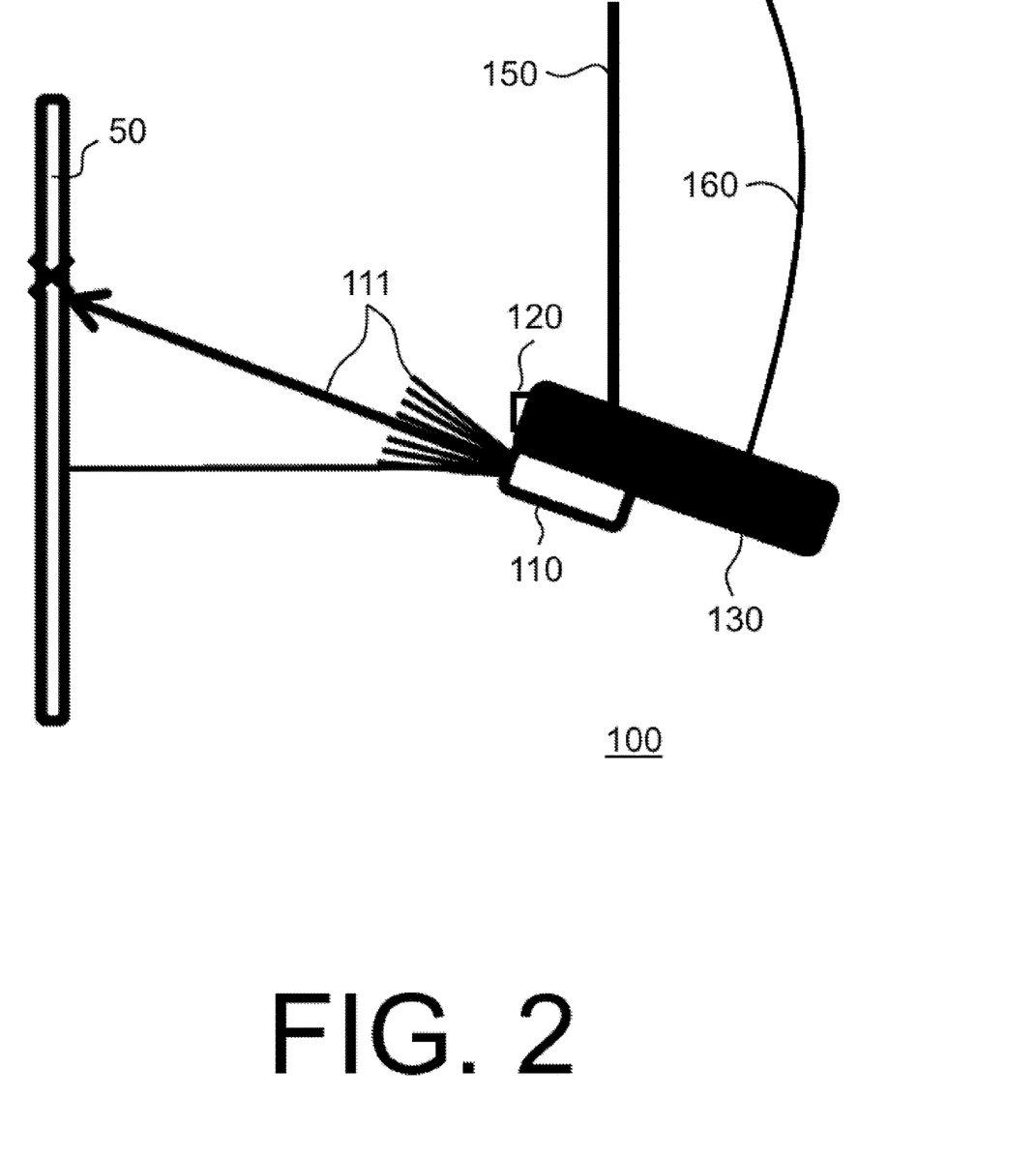
FIG. 2 is an illustration of an example embodiment nondestructive testing device.

FIG. 2 is an illustration of an example embodiment nondestructive inspection device 100 useable in a variety of environments, including in submerged nuclear reactor environments. As shown in FIG. 2, example embodiment device 100 includes an ultrasonic tester 110 that may include an ultrasonic emitter and/or sensor that uses ultrasonic vibration to detect object position within a fluid medium as well as density/material changes within objects. For example, ultrasonic tester 110 may include an ultrasonic emitter capable of emitting ultrasonic bursts 111 in frequencies and amplitudes carried by common working mediums like light or heavy water and air, as well as at least partially reflectable by denser solids. Individual bursts 111 may return data like that seen in FIG. 1 when incident on an inspection object 50, which are receivable by tester 110.

Ultrasonic tester 110 may be capable of emitting and detecting in several directions and/or in rapid sequence. For example, as shown in FIG. 2, tester 110 may emit one or more ultrasonic bursts 111 toward an object 50 to be tested. Similarly, tester 110 may be an ultrasonic phased array matrix that sequentially or simultaneously emits several bursts 111 in known orientations, angles, and/or relative positioning with respect to one another. A phased array matrix may also include matching sensors that can detect and discriminate among return bursts reflected from an object 50. A phased array matrix may also focus bursts 111 at various planes by projecting at varying pitches and angles, such that a field of emitted ultrasonic bursts 111 form an impingement field or grid at various distances and densities on object 50. Examples of phased array matrix devices that can be adapted for use as ultrasonic tester 110 include those found in US Patent Publication 2014/0060196 to FALTER et al.; US Patent Publication 2014/0036633 to Oberdorfer; US Patent Publication 2013/0220020 to Wigh et al.; US Patent Publication 2013/0197824 to Baba et al.; US Patent Publication 2011/0126626 to Koch et al.; and US Patent Publication 2009/0112094 to Qin et al., each of these publications being incorporated by reference herein in their entireties.

Example embodiment nondestructive inspection device 100 also includes a visual inspection element 120, which may be a camera. Visual inspection element 120 may be co-located with tester 110 so as to capture visual data from a same vantage as ultrasonic data being detected by tester 110. Similarly, visual inspection element 120 may be offset or fairly remote from tester 110 at a known relative distance, to permit adjusting visual data with respect to received ultrasonic testing data from tester 111. Visual inspection element 120 may be configured to operate in a working fluid, such as at extreme depths of water in a nuclear reactor environment. As such, visual inspection element 120 may be a camera sealed against higher pressures and/or hardened against irradiation or radionuclide particulate entrainment. Such a camera may include appropriate lens systems and/or lighting to capture and record and/or transmit visual data for processing or operator usage, even at great fluid depths or without external lighting.

Example embodiment nondestructive inspection device 100 may also include an orientation determinator 130, which may be an accelerometer, compass, infrared tag reader, level, GPS receiver, etc. that gives information as to position and/or orientation of device 100 with respect to a known reference frame. For example, an accelerometer oriented with tester 110 and beams 111 may use gravity to determine an absolute orientation of device 100—and ultrasonic data from tester 111 and visual data from camera 120—with respect to ground or true vertical. Rotation in other dimensions, as well as velocity or vibration, may be equally detectable with orientation determinator 130 in order to adjust, interpret, or correct data received and transmitted by device 100, as well as properly position and move device 100 for inspections.

Visual inspection element 120, tester 110, orientation determinator 130, and any other electronic component of device 100 may be locally or remotely powered. For example, as shown in FIG. 2, a power connection 160, like a cord or cable, may provide external power to aspects of example embodiment device 100. Alternately or in addition, local batteries may power, or provide backup power to, some or all components, like visual inspection element 120, a processor, orientation determinator 130, wireless communicator, tester 110, etc. Power connection 160 may also carry ultrasonic testing, orientation, command/control, and/or visual data back to an operator or processor. Still further, a wireless connector in example device 100 may transmit data between a user and device 100.

Example embodiment nondestructive inspection device 100 may be freely mobile with respect to object 50 during inspection, with or without exact position of device 100 being set or controlled. Device 100 may also include motive structures to move with respect to inspection objects 50 in a working fluid. For example, a positioning pole 150 may extend down to visual inspection device 120 and tester 110, and an operator may manipulate or move device 100 on an opposite end of pole 150. Similarly, a rope or other suspension system may be used with or for pole 150 to maneuver example embodiment devices 100 with appropriate rigging. Or, for example, a jet, propeller, or other fluid-motive or mechanical drive may be included in example device 100 to provide desired movement in a working fluid. An operator may remotely control device 100 through a same wireless data connection used for visual and ultrasonic data, permitting desired movement and orientation during inspection.

Example embodiment nondestructive inspection device 100 may further include a processor and local data store with programming and/or saved data to execute example methods discussed below. For example, a processor and appropriate memory and bus may be in a portion of element 130 in FIG. 2. As such, device 100 may be capable of processing and/or analyzing received ultrasonic, positional, and/or visual data as well as received control signals. A processor may further interpret received operational or control signals and translate the same into behaviors of tester 110, visual inspection device 120, a movement drive, determinator 130, data transmitter, etc.

Example embodiments can be used in a variety of ways to perform visual and nondestructive testing of components. For example, in a nuclear power plant, like a BWR, ESBWR, PWR, CANDU, or ABWR, areas, like underwater next to a component weld or in a spent fuel pool, example embodiment devices may be introduced to visually and/or ultrasonically test components for placement, internal integrity, shape, appearance, etc., with or without regard for set positioning of example embodiment devices. Example embodiment devices may also be used in conjunction with example methods discussed below, such as through appropriate programming or operator action. However, example embodiment devices may also engage in other behaviors and activities useful in inspection environments.

Example Methods

Figure 3:
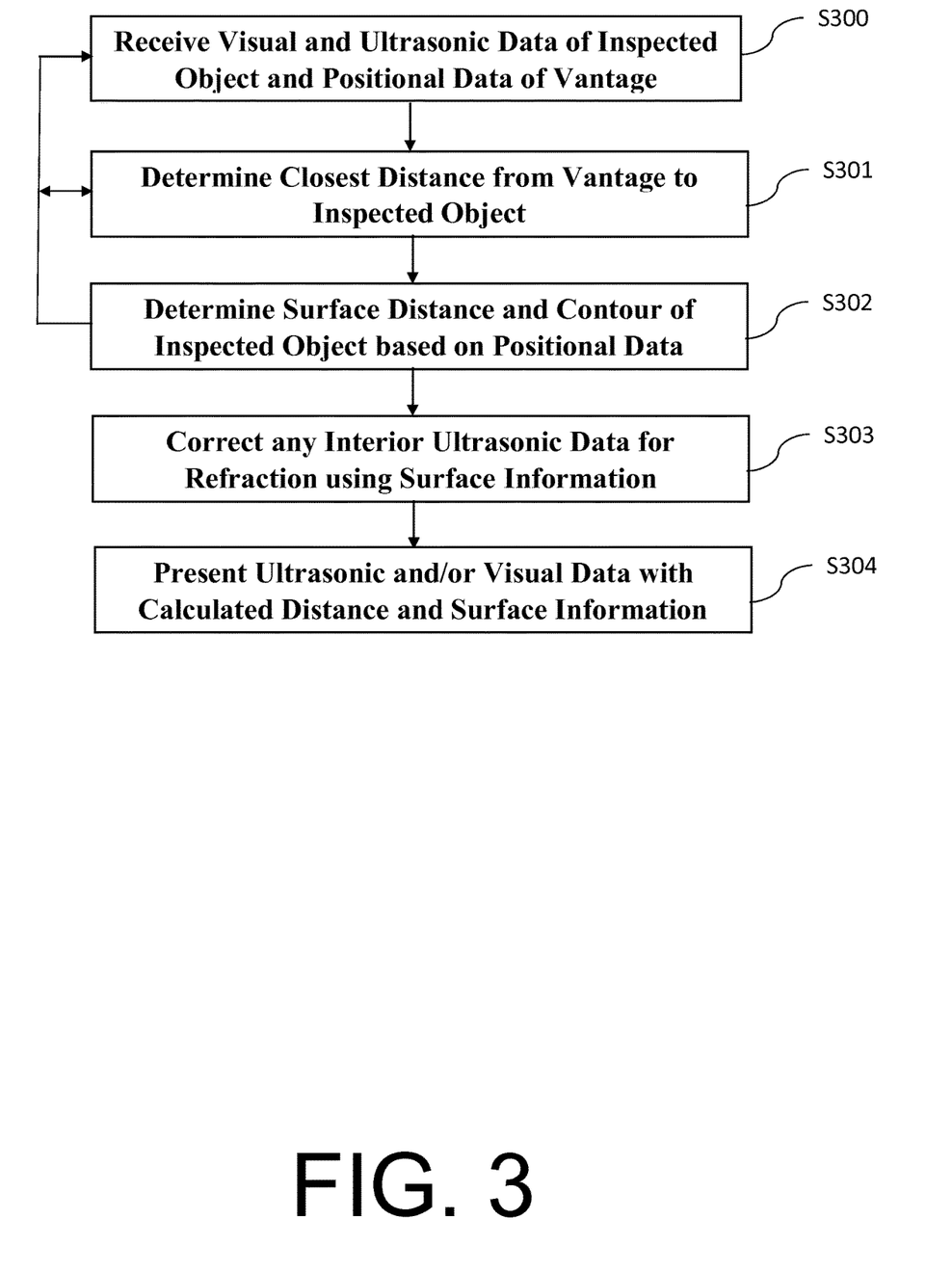
FIG. 3 is a flowchart of an example method of nondestructive testing.

FIG. 3 is a flowchart illustrating an example method of nondestructive testing using a testing device. As shown in FIG. 3, in S300 visual, ultrasonic testing, and/or positional data are received from appropriate detector(s), like an ultrasonic testing device. For example, using an example embodiment device shown in FIG. 4, a user maneuvering the device about component 50 may collect data from tester 110, camera 120, accelerometer 130, etc. being operated in a fluid medium in which component 50 is immersed. Alternatively, orientation data could be derived from image processing on visual data alone, or visual data could be reconstructed from received ultrasonic testing data. As such, the visual, ultrasonic, and positional data may come from several different sources and even be derived from one-another. In S300, data may be retrieved in real-time and simultaneously, such as ultrasonic pings being detected and associated with particular video frames and accelerometer outputs. Or, in S300, different types of data may be received asynchronously and stored or otherwise used at later points in time as other data is received.

Figure 4:
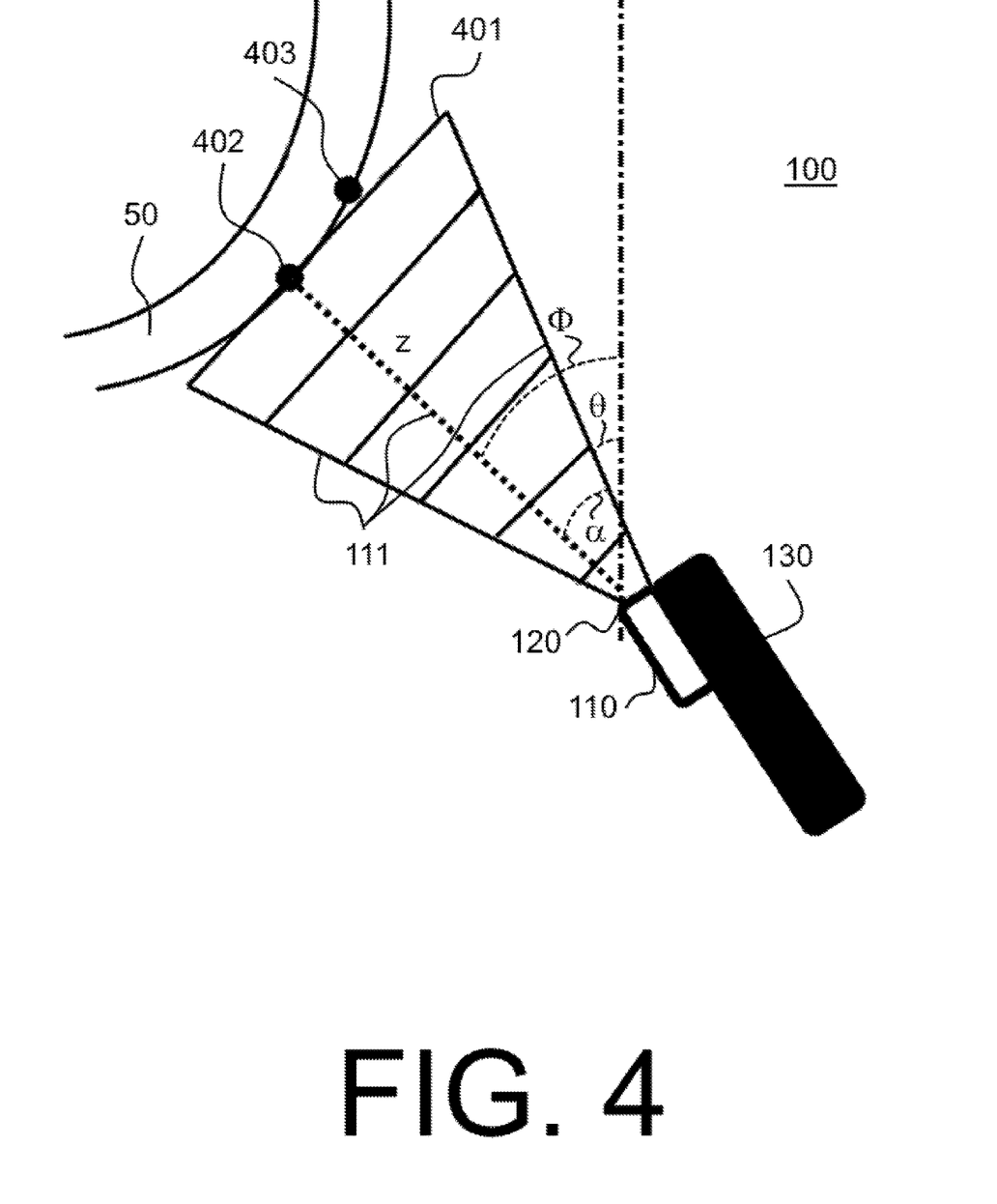
FIG. 4 is an illustration of an example embodiment nondestructive testing device in use with example methods.

In S301, a distance to a closest point and thus working plane is determined using at least some data received in S300. For example, using an example embodiment ultrasonic testing device of FIG. 4, a working plane 401 may be a plane tangent to a closest detection point 402 from a vantage. In FIG. 4, the vantage is tester 110 and camera 120 receiving visual and ultrasonic data at a same point, but separated and different vantages may be used in example methods with appropriate accommodation for separation between vantages. Because closest point 402 is a smallest distance away, ultrasonic signals received from emitted beams 111 may be strongest and/or fastest reflected back to a sensor and detected from closest point 402. By identifying a strongest signal among several ultrasonic bursts 111 emitted in several directions to working plane 401, such as among those emitted by a phased array matrix focused on working plane 401, a distance from the vantage to object 50 can be determined with the known speed of sound in the working medium. For example, a ping 111 first received back at 0.67 milliseconds may correspond to a distance of approximately 0.5 m for "z" in water—the distance to closest point 402 and working plane 401 in FIG. 4. Of course, other calculations and data may be used in determining object minimum distance in S301, such as image analysis or mechanical measurement of distance between any vantage and an object being inspected.

S301 and S300 may be repeated to ensure that a true, closest point from a vantage and working plane is identified and determined. Through spurious movement of a vantage, too coarse or incorrect focusing of ultrasonic bursts, and/or interpositioning of unwanted or transient objects, a fastest ping received in S300 may not actually correlate with reflection from a closest point. For example, if bursts 111 in FIG. 4 are emitted at larger angular intervals, point 402 may not be intersected and instead point 403 may be the fastest reflection point, resulting in an incorrect identification of a closest point and measurement of distance to a working plane. Refocusing of tester 110 and/or multiple rounds and gradients of emitting bursts 111 may uncover faster pings from point 402, which can then be identified as the closest point and used to determine distance "z" to true working plane 401. Multiple passes of S301 and S300 may be conducted to ensure a closest working plane is consistently identified and measured for distance.

In S302, positional data is used to derive length and orientation of the working plane, and, by successively moving the working plane to farther points on an object, to determine relative distances of several points on the inspected object and thus its surface contours. Using the example of FIG. 4, angle α may be known based on specifications and operation of tester 110. For example, if tester 110 is a phased array matrix ultrasonic emitter, each of several beams 111 may be emitted at a known angle α from a cone having a known maximum sweep from tester 110; or, if a simple ultrasonic emitter is used sequentially at several angles, emission angles of each beam 111 will be known with respect to tester 110 as each is emitted. Angle θ can be determined from positional data.

For example, using accelerometer 130 in a proper orientation, an angle between tester 110 and absolute (gravitational) vertical can be determined and thus the angle θ with the maximum sweep of tester 110. Or, for example, positional data may include only visual and ultrasonic data that can be used to determine relative positioning and striking angles through image processing, using methods like Structure-From-Motion. Knowing the angle θ between tester 110 and vertical and the relative angle a of each beam 111 with respect to tester 110, an absolute angle Φ of each beam 111 with respect to the vertical can be determined. For a beam from the working plane 401 along distance z, knowing Φ and distance z permits calculation of a length of plane 401 as well as any distance along any beam 111 to working plane 401 from a sweep of tester 110.

S300-S302 may be repeated at multiple depths or using different focuses of ultrasonic testing pulses in order to map out a surface of an object being inspected. For example, beams 111 of tester 110 may be refocused in the instance a phased array matrix is used to move working plane 401 to further point 403, which is known to be farther away than closest point 402 based on the identification of 402 as a closest point in S301. An ultrasonic beam 111 may be directed at farther point 403 to confirm its distance, and orientation data from accelerometer 130 and tester 110 or other positional data can determine its distance. Through successive identification of surface points and calculation of their true distance from a vantage, a continuous surface contour, with incident angles and distances, of object 50 may be mapped out. Similarly, positional data derived from visual information using Structure-From-Motion methods coupled with calculated distances from ultrasonic data can be used to determine surface information.

In S303, ultrasonic data may be corrected if it comes from positions internal to an inspected object as determined by the contour in S302. That is, in S300-S302, ultrasonic data and positional data was used to determine distance and shape of an inspected object's surface, but in S303, ultrasonic data is additionally gathered and corrected for internal nondestructive testing purposes. When a working plane is advanced beyond a closest point of an inspected object, some ultrasonic reflections of beams focused beyond the closest point may come from inside the object. This may result in ultrasonic pulses moving from a fluid working medium through a solid component and back, or through any two materials with differing densities/speeds of sound. When moving through multiple media having varying speeds of sound, ultrasonic waves will refract in proportion to the ratio of the speeds of sound in the media. That is, the ultrasonic beams being reflected from internal points, such as when a working plane is moved or a phased matrix array is refocused to internal locations, will reorient due to differences in density between a working medium and material in an object being inspected. Correcting this change in S303 may make use of the surface contours mapped in S302. The change in beam direction is known by relationship of Snell's Law as $\sin(\theta_{ext}) \cdot V_{ext}/V_{int} = \sin(\theta_{int})$, where $\theta_{ext}$ is the external incidence angle, $V_{ext}$ is the speed of the ultrasonic burst in the exterior medium, $V_{int}$ is the speed of the ultrasonic burst in the interior medium, and $\theta_{int}$ is the mirror internal incidence angle.

Using FIG. 4 as an example of S303, the surface and relative distances to tester 110 from object 50 may be known from S302. Also knowing the absolute angle Φ and focus/depth z, one can determine the striking angle of each beam 111 on object 50. The speeds of ultrasonic pulses in a working medium like water and object 50 may be known or directly tested during inspections. As working plane 401 is advanced beyond closest point 402, beams 111 may be focused within, and return data with, interior of object 50. However, angles of beams 111 may change as they refract into and reflect back through object 50. Knowing the incidence angle, velocities, and distances between vantage and reflection/data point interior to object 50 from prior actions, the change in angles of beams 111 may be corrected in S303 using the relationship given above. By applying this treatment to identified interior ultrasonic data, on can know the true position of any reflection point in object 50 and thus correctly associate ultrasonic testing results with position in an object.

In S304, the collected, and potentially corrected, ultrasonic data and calculated distances/surface information may be presented to a user, potentially correlated with visual data. For example, if visual data from a camera 120 in FIG. 4 is synchronized temporally and spatially with corrected ultrasonic data from a tester 110 gathered and calculated in S300-S303, then visual data returned by camera 120 may be augmented with a point cloud or data/color overlay of distances to particular objects or even pixels. Similarly, calculated distances and surface information may be presented with such visual data, like true positioning of material edges and thicknesses.

Of course, all types of received data and calculated information may also be presented together in S304. For example, visual data may include distance and/or other positional information overlaid as data points along with a color coded overlay showing ultrasonic results, and potentially cracks or other internal disruptions, in sync with the visual data. In this way, a user may be able to instantly know how far away, and/or at what angle from a vantage, a particular visual feature is on a camera feed inspecting an object. The user may also be provided with internal information about visual features, permitting an easy correlation between potential flaws or internal boundaries and external object locations. Providing this information in example methods may not require strict positioning or location tracking of any ultrasonic testing device, because such relative and absolute positional and distance information can be derived by example methods.

Example embodiments and methods thus being described, it will be appreciated by one skilled in the art that example embodiments may be varied and substituted through routine experimentation while still falling within the scope of the following claims. For example, while an example embodiment may use water as a working medium in a nuclear power plant to inspect a solid metallic component, it is understood that other example embodiments are useable in air and with multiple components of intermediate densities by accounting for the differing speeds of sound in these media. All such changes fall within the scope of the following claims, and such variations are not to be regarded as departure from the scope of the following claims.

What is claimed is:

1. A device for nondestructive testing of an object, the device comprising:
   a nondestructive testing emitter and receiver;
   a locator configured to determine a position of the nondestructive emitter and receiver relative to the object;
   a movement structure, wherein the emitter and receiver, the locator, and the movement structure are freely moveable in all directions with respect to the object being tested; and
   a computer processor configured to,
      receive, from the emitter and receiver, ultrasonic data reflected from the object in a working fluid and, from the locator, positional data of a point of reception of the ultrasonic data,
      determine a closest point between the object and the point and a distance between the object and the point using the ultrasonic data,
      determine a surface of the object being tested using the closest point, at least one farther point, and the positional data,
      correct the ultrasonic data if the ultrasonic data is internal to the object, wherein the correcting uses the speed of emitted beams from the tester in the working fluid, a speed of the beams in the object, and an angle of incidence of the beams on the object calculated from the surface and the positional data, and
      transmit the ultrasonic data with at least one of the determined surface and the distance.

2. The device of claim 1, wherein the nondestructive testing emitter and receiver is an ultrasonic emitter and receiver using ultrasonic energy that reflects from the object being tested.

3. The device of claim 1, wherein the locator is an accelerometer rigidly affixed with the emitter and receiver, and wherein the accelerometer is configured to determine an orientation of the emitter and receiver with respect to a vertical.

4. The device of claim 1, further comprising:
   a visual inspection device, wherein the emitter and receiver, the locator, and the movement structure are all configured to be immersed and function in a working fluid with the object.

5. The device of claim 4, wherein,
   the visual inspection device is a camera configured to capture video of the object,
   the nondestructive testing emitter and receiver is an ultrasonic emitter and receiver,
   the locator is an accelerometer, and
   the camera, the ultrasonic emitter and receiver, and the accelerometer are configured to be submerged and operable in water in a radioactive environment.

6. The device of claim 5, wherein the movement structure is at least one of a pole and a rope extending from operators above the water to the device.

7. The device of claim 5, further comprising:
   a local power supply; and
   a communications transmitter and receiver.

8. The device of claim 1, wherein the nondestructive testing emitter and receiver is a phased array matrix configured to emit a plurality of discreet ultrasonic bursts that may be focused at different planes in the object being tested.

9. A device for nondestructive testing of an object, the device comprising:
   a phased array ultrasonic emitter;
   a camera, wherein the phased array ultrasonic emitter and the camera are freely moveable together; and
   a computer processor configured to,
      receive, from the phased array ultrasonic emitter, ultrasonic data reflected from the object in a working fluid and positional data of a point of reception of the ultrasonic data,
      determine a closest point between the object and the point and a distance between the object and the point using the ultrasonic data,
      determine a surface of the object being tested using the closest point, at least one farther point, and image data from the camera,
      correct the ultrasonic data if the ultrasonic data is internal to the object, wherein the correcting uses the speed of emitted beams from the tester in a working fluid, a speed of the beams in the object, and an angle of incidence of the beams on the object calculated from the surface and the positional data, and
      transmit the ultrasonic data with at least one of the determined surface and the distance.

10. The device of claim 9, further comprising:
    an accelerometer paired with the emitter, wherein the accelerometer is configured to determine an orientation of the emitter;
    a communications connection configured to transmit data from and provide power to the emitter, processor, accelerometer, and camera; and
    a rod rigidly connected to the emitter, the accelerometer and the camera and extending remotely to permit a user to move the emitter, the accelerometer, and the camera.

11. The device of claim 10, wherein the communication connection, rod, emitter, accelerometer, and camera are configured to be submerged in water in a radioactive environment without losing operational capacity or entraining radioactive particles.

12. A method of freeform nondestructive testing, the method comprising:
    receiving ultrasonic data reflected from an object being tested in a working fluid and positional data of a point of reception of the ultrasonic data, wherein the receiving is executed with a phased array ultrasonics tester at the point of reception;
    determining a closest point between the object and the point and a distance between the object and the point using the ultrasonic data;
    determining a surface of the object being tested using the closest point, at least one farther point, and the positional data, wherein the determining the surface is executed with the tester by sequentially refocusing the tester beyond the closest point;
    determining if the ultrasonic data is internal to the object based on the determined surface and a distance of a focus of the tester;
    correcting the ultrasonic data if the ultrasonic data is internal to the object, wherein the correcting uses the speed of emitted beams from the tester in the working fluid, a speed of the beams in the object, and an angle of incidence of the beams on the object calculated from the surface and the positional data; and
    presenting the ultrasonic data with at least one of the determined surface and the distance.

13. The method of claim 12, further comprising:
    capturing video of the object at the same time as the receiving ultrasonic data.

14. The method of claim 13, wherein the ultrasonic data and the at least one of the determined surface and the distance is presented with the video in temporal and spatial sync with the video such that the object in the video is annotated with the ultrasonic data and the at least one of the determined surface and the distance at corresponding pixels.

15. The method of claim 14, wherein the capturing is executed with a camera rigidly positioned with the point of reception.

16. The method of claim 15, wherein the receiving is executed with a phased array ultrasonics tester at the point of reception, and wherein the camera and the tester are rigidly positioned together with a movement structure in a nondestructive testing device, the method further comprising:

moving the point of reception and the nondestructive testing device relative to the object without directly contacting any solid in the working fluid with the device.

* * * * *